Feb. 20, 1973 W. E. RUNKEL Plant Pat. 3,308
APPLE TREE
Filed April 9, 1971
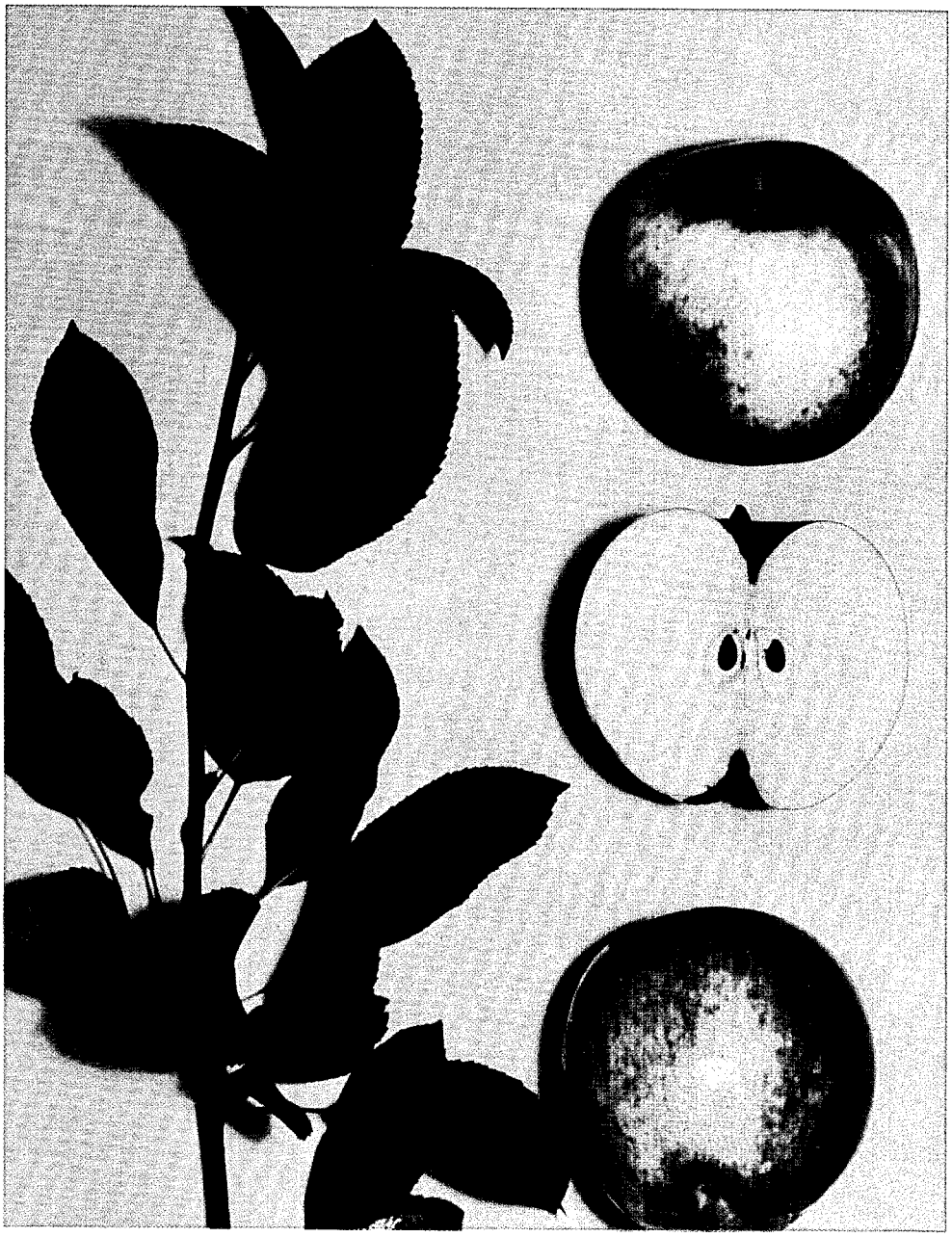
Walter E. Runkel
INVENTOR.
BY Clarence A. O'Brien and Harvey B. Jacobson
Attorneys

United States Patent Office

Plant Pat. 3,308
Patented Feb. 20, 1973

3,308

APPLE TREE

Walter E. Runkel, 19368 Midway Ave., Southfield, Mich. 48075

Filed Apr. 9, 1971, Ser. No. 132,922
Int. Cl. A01h 5/03
U.S. Cl. Plt.—34 1 Claim The present invention relates to a new and distinct variety of apple tree which was discovered by me as a newly found seedling of unknown parentage on my cultivated property in the city of Southfield, Oakland County, Mich.

At the time of my discovery aforementioned, my attention was attracted to this new seedling by reason of the fact that it bore large flavorful red apples. Originally, ths seedling had come up from a seed on my cultivated property at 613 Part Street, Lincoln Park, Mich., and later I moved it along with other seedlings and bushes to its present location. When it eventually bore fruit, I recognized the fact that I had a valuable tree.

Apparently the tree is a cross between a Delicious apple and some other variety. The fruit is large, bright red, very juicy, and very flavorful, with a distinctive rich sweet taste. Also, I have found this apple to have other desirable features; it has excellent keeping qualities, and shows no tendency to shrivel in storage. The most important characteristic, however, is the taste, which I consider unique and distinctive, unmatched by any other apple.

Asexual reproduction of my new variety, as performed by grafting, on my property in Southfield, confirmed that the foregoing characteristics come true and are established and transmitted through succeeding propagations. Despite the uncertainty of the parentage of my new seedling, I believe that it represents a new and distinct variety by the unique combination of characteristics referred to in the foregoing.

The accompanying illustrations show typical specimens of the fruit and foliage of my new variety of Apple Tree as depicted in color as nearly true as is reasonably possible to make the same in a color illustration of this character, with certain of the fruit specimens being shown in cross section.

The following is a detailed description of my new variety, with terminology in accordance with the Munsell Color chart, except where general color terms of ordinary dictionary significance are obvious:

Locality where grown and observed: 19368 Midway, city of Southfield, Oakland County, Mich.

*Tree:*

*Size.*—Medium; upright; round-topped; vigorous; hardy, rapid growing; very productive; regular bearer.

*Trunk.*—Stocky; medium shaggy.

*Branches.*—Smooth; medium thickness; much-branched.

*Color.*—Reddish brown; Munsell Plate 7.5 YR 3/4.

*Lenticels.*—Medium number; medium size.

*Leaves.*—Large; long (about 5½ inches); medium width (about 2 inches); elliptical; tips acute, taper-pointed; bases rounded; slightly rugose; thin; medium number; smooth; glabrous.

*Color.*—Medium green, Munsell Plate 2.5 GY 5/6. Margin—serrate. Petiole—medium length (about 1¼ inches); slender; pubescent. Stipules—very small.

*Flowers:*

Blooms at the same time as other varieties (Golden Delicious, Jonathan). Large. Color—white petals with pink veins. Dates of first and full bloom—May 1 and May 9, respectively.

*Fruit:*

*Size.*—Uniform. Axial diameter—about 2¾ inches; transverse diameter—about 3¼ inches.

*Form.*—Symmetrical; regular; round-oblate to round-conic.

*Specific gravity.*—Heavy; compact; hard.

*Cavity.*—Symmetrical; regular; even; smooth; acute; angle of shoulder—smoothly rounded. Width—medium (about 1⅜); depth—medium about (½ inch). Markings—sometimes russeted with radiating lines, otherwise unmarked.

*Stem.*—Erect; thickness—medium to thick (about 5/32 inch); short (about ⅜ to ½ inch); clubbed at tip end.

*Basin.* — Symmetrical; abrupt; furrowed; shoulder crowned by five small but distinct points. Depth—medium to shallow (about ¼ inch); width—narrow (about 1 inch). Markings—none; red pigment extends completely into basin—the usual greenish skin in the basin is absent.

*Calyx.*—Somewhat open to closed; small (about ¼ inch in diameter); pubescent. Lobes—connivent with reflexed tips; loose at tips; medium size about (3/16 inch); narrow; acuminate.

*Skin.*—Thin; tender; smooth; bright; waxen. Dots—rather conspicuous; few; large; even; circular; none or almost none at calyx end; color—russet. Ground color—greenish yellow, Munsell Plate 2.5 GY 9/6. Color markings—splashed; self-colored; bright. Color—pinkish-red, Munsell Plate 7.5 R 3/12. Bloom—wanting. Scarskin—wanting.

*Flesh.*—Very juicy. Color—yellowish cream. Texture—tender; medium; crisp; firm. Flavor—mildly subacid; rich; sweet. Aroma—distinct. Quality—very good.

*Core.* — Median. Bundle — inconspicuous, in one whorl. Color—yellowish green. Alternate bundle—approximate to tubes below stamens. Core lines—meeting; distinct in cross section. Carpellary area—medium in size; distinct. Calyx tube—funnel-shaped; long (about 7/16 inch); narrow (about 5/32 inch). Styles—present; distinct to base; pubescent towards base. Stamens—median; in a distinct whorl. Axillary cavity—present. Seed cells—closed; cell walls—thick; length—about ¾ inch; breath—about ⅜ inch. Shape — roundish cordate. Cross section—board (about ⅞ inch). Surface—fissured; slightly tufted.

*Seeds.*—Average number—9. Length about 5/16 inch. Breath about 3/16 inch. Form—acute; plump. Color—dark brown.

*Use.*—Fresh eating, salads, pies, baked, dumplings, sauce.

*Keeping quality.*—Very good; keeps in excess of 180 days in regular storage. Shows no tendency to shrivel.

*Ripening.*—Ripens from the inside out; core area becomes ripe before the other flesh. Subject to water core.

*Pest resistance.*—Resistance to both insects and diseases was found to be as good as other varieties of apple trees grown on the same property and under the same conditions.

Having thus disclosed my invention, I claim:

1. A new and distinct variety of apple tree, substantially as herein shown and described, characterized particularly as to novelty by the unique and distinctive rich flavor of the fruit; and further characterized by the long keeping quality of the fruit in storage with no tendency to shrivel.

No references cited.

ROBERT E. BAGWILL, Primary Examiner